US006803199B2

(12) United States Patent
Carrasco et al.

(10) Patent No.: US 6,803,199 B2
(45) Date of Patent: Oct. 12, 2004

(54) THYROID SODIUM/IODIDE SYMPORTER AND NUCLEIC ACID ENCODING SAME

(75) Inventors: Nancy Carrasco, Bronx, NY (US); Ge Dai, Bronx, NY (US); Orlie Levy, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 15 days.

(21) Appl. No.: 09/995,007

(22) Filed: Nov. 26, 2001

(65) Prior Publication Data

US 2002/0123102 A1 Sep. 5, 2002

Related U.S. Application Data

(63) Continuation of application No. 08/595,553, filed on Feb. 1, 1996, now Pat. No. 6,391,579.

(51) Int. Cl.[7] .......................... C12Q 1/68; G01N 33/53; C07H 21/04
(52) U.S. Cl. ........................... 435/6; 435/7.1; 536/23.1; 536/23.5; 536/24.1; 536/24.3; 530/300; 530/350; 530/387.1
(58) Field of Search ........................... 435/6, 7.1, 69.1, 435/252.3, 320.1; 536/23.1, 23.5, 24.1, 24.3, 23.6, 24.31; 530/300, 350, 387.1

(56) References Cited

U.S. PATENT DOCUMENTS 6,391,579 B1   5/2002   Carrasco et al.

OTHER PUBLICATIONS

Vilijin, F et al. "Expression of the Thyroid Sodium/Iodide Symporter in Xenopus laevis Oocytes," The Journal of Biological Chemistry, vol. 264, No. 20, Jul. 15, 1989, pp. 11901–11903.*

Bonaldo, ME et al., "Normalization and subtraction: two approaches to facilitate gene discovery," Genome Research, 1996, Vo 6, pp. 791–806.*

Manlatis et al (1982) Molecular Cloning A Laboratory Manual. Cold Spring Harbor Laboratory. pp. 217–218, 248–251 and 412–413.

Hediger et al. (1987) Expression cloning and cDNA sequencing of the Na+/glucose co–transporter. \Nature, vol. 330, pp. 379–381.

Guastella et al. Cloning and Expression of a Rat Brain GABA Transporter. (1990) Science, vol. 249, pp. 1303–1306.

Russell et al. "Protein 618 AA"; Database: A_Geneseq_0601: Accession No.: AAB73921: May 29, 2001.

* cited by examiner

Primary Examiner—Carla J. Myers
Assistant Examiner—Alexander H. Spiegler
(74) Attorney, Agent, or Firm—Amster, Rothstein & Ebenstein LLP

(57) ABSTRACT

The present invention provides a purified and isolated nucleic acid encoding a sodium/iodide symporter. The present invention also provides purified sodium/iodide symporter, a vector comprising nucleic acid encoding sodium/iodide symporter, a host cell transformed with the vector, and a method for producing recombinant sodium/iodide symporter. In addition, the present invention provides nucleic acid probes and mixtures thereof specific for sodium/iodide symporter nucleic acid and antibodies immunoreactive with sodium/iodide symporter. The present invention also provides a method for diagnosing and treating thyroid disorders associated with non-functional sodium/iodide symporter. Furthermore, the present invention provides a method for the selective ablation of tissue. The present invention also provides a method for identifying an iodide transport protein in non-thyroid tissue. Finally, the present invention provides a non-human, transgenic model for a thyroid disorder.

15 Claims, 8 Drawing Sheets

```
gaattccgggtcgaccacgcgtccggcggtgactcgcgctgcgactctcccactgaccga    60
gagtcccgacgtcctccgcatcctctcctcaccgagtcacctgtctccATGGAGGGTGC   120
                                                M  E  G  A    4
GGAGGCCGGGCCCGGGCCACCTTCGGCGCCTGGGACTACGGCGTGTTCGCGACCATGCT   180
 E  A  G  A  R  A  T  F  G  A  W  D  Y  G  V  F  A  T  M  L   24
GCTGGTGTCCACGGGCATCGGGCTATGGGTCGGCCTGGCCCGCGGTGGCCAACGCAGTGC   240
 L  V  S  T  G  I  G  L  W  V  G  L  A  R  G  G  Q  R  S  A   44
CGACGACTTCTTTACCGGGGGCCGGCAGTTGGCAGCCGTTCCTGTGGGCTGTCGCTGGC   300
 D  D  F  F  T  G  G  R  Q  L  A  A  V  P  V  G  L  S  L  A   64
CGCCAGTTTCATGTCGGCTGTGCAGGTGCTCGGGGTCCCCGCCGAGGCAGCGCGCTACGG   360
 A  A  V  F  M  S  A  V  Q  V  L  G  V  P  A  E  A  A  R  Y  G 84
GCTCAAGTTCCTGTGGATGTGCGCGGGTCAGTTGCTCAACTCGCTGCTCACAGCGTTTCT   420
 L  K  F  L  W  M  C  A  G  Q  L  N  S  L  L  T  A  F  L   104
CTTCTTGCCGATCTTCTACCGCCTGGGCCTTACCAGCACCTACCAGTACCTAGAGCTGCG   480
 F  L  P  I  F  Y  R  L  G  L  T  S  T  Y  Q  Y  L  E  L  R   124
CTTCAGCCGAGCGGTCCGGCTCTGCGGGACGCTGCAGTACTTGGTGGCCACGATGCTGTA   540
 F  S  R  A  V  R  L  C  G  T  L  Q  Y  L  V  A  T  M  L  Y   144
TACAGGCATCGTGATCTACGCGCCTGCGCTCATCCTGAACCAAGTGACCGGGTTGGACAT   600
 T  G  I  V  I  Y  A  P  A  L  I  L  N  Q  V  T  G  L  D  I   164
CTGGGCATCGCTCCTGTCCACAGGAATCATCTGCACCTTGTACACTACCGTGGGTGGTAT   660
 W  A  S  L  L  S  T  G  I  I  C  T  L  Y  T  T  V  G  G  M   184
GAAGGCCGTGGTCTGGACAGATGTGTTCCAGGTTGTGGTAATGCTCGTTGGCTTCTGGGT   720
 K  A  V  V  W  T  D  V  F  Q  V  V  V  M  L  V  G  F  W  V   204
GATCCTGGCCCGAGGCGTCATTCTCCTGGGGGGTCCCCGGAACGTGCTCAGCCTCGCTCA   780
 I  L  A  R  G  V  I  L  L  G  G  P  R  N  V  L  S  L  A  Q   224
GAACCATTCCCGGATCAACCTGATGGACTTTGACCCTGATCCTCGGAGCCGGTACACCTT   840
 N  H  S  R  I  N  L  M  D  F  D  P  D  P  R  S  R  Y  T  F   244
CTGGACTTTCATAGTGGGTGGCACACTGGTGTGGCTCTCCATGTACGGTGTGAACCAAGC   900
 W  T  F  I  V  G  G  T  L  V  W  L  S  M  Y  G  V  N  Q  A   264
CCAGGTACAGCGCTATGTGGCCTGCCACACAGAGGGAAAGGCCAAACTGGCCCTGCTTGT   960
 Q  V  Q  R  Y  V  A  C  H  T  E  G  K  A  K  L  A  L  L  V   284
CAACCAGCTGGGCCTCTTCCTGATTGTGGCCAGTGCAGCCTTGCTGTGGCATTGTCATGTT  1020
 N  Q  L  G  L  F  L  I  V  A  S  A  A  C  C  G  I  V  M  F   304
CGTCTACTACAAGGACTGTGACCCCCTCCTCACAGGCCGTATCTCAGCCCCCGACCAGTA  1080
 V  Y  Y  K  D  C  D  P  L  L  T  G  R  I  S  A  P  D  Q  Y   324
CATGCCGCTGCTTGTGTTGGACATTTTTGAGGATCTGCCCGGGGTCCCCGGGCTCTTCCT  1140
 M  P  L  L  V  L  D  I  F  E  D  L  P  G  V  P  G  L  F  L   344
GGCCTGTGCCTACAGTGGCACCCTCAGCACTGCATCCACCAGCATCAACGCCATGGCAGC  1200
 A  C  A  Y  S  G  T  L  S  T  A  S  T  S  I  N  A  M  A  A   364
TGTGACTGTGGAAGACCTCATCAAGCCGAGGATGCCTGGCCTGGCACCTCGGAAGTTGGT  1260
 V  T  V  E  D  L  I  K  P  R  M  P  G  L  A  P  R  K  L  V   384
TTTCATCTCTAAAGGGCTCTCATTCATCTACGGCTCTGCCTGCCTCACTGTGGCTGCTCT  1320
 F  I  S  K  G  L  S  F  I  Y  G  S  A  C  L  T  V  A  A  L   404
GTCCTCACTGCTGGGAGGTGGTGTCCTCCAGGGTTCCTTCACTGTGATGGGTGTCATCAG  1380
 S  S  L  L  G  G  G  V  L  Q  G  S  F  T  V  M  G  V  I  S   424
TGGGCCTCTACTAGGCGCCTTCACGCTTGGGATGCTGCCCAGCCTGCAACACGCCAGG    1440
 G  P  L  G  A  F  T  L  G  M  L  P  A  C  N  T  P  G         444
CGTTCTCTCCGGGTTGGCAGCAGGCTTGGCTGTATCCCTGTGGGTGCCCGTAGGGGCCAC  1500
 V  L  S  G  L  A  A  G  L  A  V  S  L  W  V  A  V  G  A  T   464
ACTGTATCCCCCTGGAGAGCAGACCATGGGGGTGCCTCCCACCTCGGCTGCAGGCTCAC   1560
 L  Y  P  P  G  E  Q  T  M  G  V  L  P  T  S  A  A  G  C  T   484
CAACGATTCGGTCCTCCTGGGCCCACCTGGAGCCACCAACGCTTCCAACGGGATCCCAG   1620
 N  D  S  V  L  L  G  P  P  G  A  T  N  A  S  N  G  I  P  S   504
TTCTGGAATGGACACGGGCCGCCCTGCCCTCGCTGATACCTTTTACGCCATCTCCTATCT  1680
 S  G  M  D  T  G  R  P  A  L  A  D  T  F  Y  A  I  S  Y  L   524
CTATTACGGGGCTCTGGGCACGCTGACCACCATGCTTTGCGGTGCTCTCATCAGCTACCT  1740
 Y  Y  G  A  L  G  T  L  T  T  M  L  C  G  A  L  I  S  Y  L   544
TACTGGTCCCACCAAGCGCAGCTCCCTGGGTCCCGGATTGCTGTGGTGGGACCTTGCTCG  1800
 T  G  P  T  K  R  S  S  L  G  P  G  L  L  W  W  D  L  A  R   564
ACAGACAGCGTCTGTGGCCCCAAAGGAAGACACTGCCACCCTGGAGGAGAGCCTGGTGAA  1860
 Q  T  A  S  V  A  P  K  E  D  T  A  T  L  E  E  S  L  V  K   584
GGGACCGGAAGACATCCCTGCTGTGACCAAGAAGCCCCCTGGCCTCAAGCCAGGCGCCGA  1920
 G  P  E  D  I  P  A  V  T  K  K  P  P  G  L  K  P  G  A  E   604
GACCCACCCCCTGTATCTGGGGCACGATGTGGAGACCAACCTCtgagggcggggtccaag  1980
 T  H  P  L  Y  L  G  H  D  V  E  T  N  L                      618
aaggccaatcacaggcctcgggccagcagcctcctctctggatggttggacctgagcata  2040
tatagaagcttggctgatacatgcctgcccagaagtccctgtgtcttacccgcaccaaa   2100
gagagagagagagagagagagagagagagagagagagagaggagttggttctccatcc    2160
acaaaggaaaccgtctggaaccttcatgcccttgtagatttcagtaggcagcggagaaca  2220
ctcagcttctccagactgaggttttctcatttatcaggcagagaaacggagggctgtcac  2280
cccaacaccggggaggagacagtagaagggtcatagatacaaagaaaactaaggcagagg  2340
gagaaatgaattgtctacagagcacagagctccaaggattgtgaagctaccttgaggtgc  2400
caagggacggattctcagagccttcacaagacacaaacgacgagttgcctcctccaatt   2460
cagatggtttgcagactatcagagaacatgtttcctgtgattcagctacctagcctctg   2520
ccaacgtgttccagcttccaggaggccacacagaccccaccccccatgctctcaccctt   2580
acccctgtgcttttcacacactaggcaactgctccaccacaggacctcacacctagacct  2640
ccgtttttgacacagggccttaaggtaatctggctgccatctgactatctctcagcacgt  2700
tcacgtacaatatttcattcttttttcattgccaagttgtcttgtaaggagagaccaca   2760
AtgtgtcatccatgcccagcttttgtgtctaacaAataaaatcgctgaaggtgttcaggt  2820
gcaatggcctgtgacatta
```

FIG. 2

THYROID SODIUM/IODIDE SYMPORTER AND NUCLEIC ACID ENCODING SAME

This application is a continuation of U.S. patent application Ser. No. 08/595,553, filed Feb. 1, 1996, now U.S. Pat. No. 6,391,579 B1, issued May 21, 2002, the contents of which are hereby incorporated by reference.

STATEMENT OF GOVERNMENT INTEREST

This invention was made with government support under NIH Grant No. DK-41544. As such, the government has certain rights in this invention.

BACKGROUND OF THE INVENTION

The principal function of the thyroid gland is to produce the hormones thyroxine (tetraiodothyronine, $T_4$) and tri-iodothyronine ($T_3$), both of which play essential roles in regulating intermediary metabolism in virtually all tissues and in maturation of the nervous system, skeletal muscle and lungs in the developing fetus and the newborn (Werner and Ingbar, *The Thyroid: A fundamental and clinical text* (Braverman and Utiger, eds.) (1991) pp. 1–1362, Lippincott, Philadelphia; DeGroot, *Endocrinology* (DeGroot, ed.) (1995) Grune and Stratton, Orlando, Fla.). Thyroxine and $T_3$ are unique hormones in that both contain iodine as an essential constituent.

The hormone-producing thyroid follicular cells or thyrocytes display a highly specialized ability to transport iodide, the anionic form of iodine. This ability is an apparent cellular adaptation to sequester environmentally scarce iodine, thus ensuring adequate thyroid hormone production in most cases. Nevertheless, insufficient dietary supply of iodine is still prevalent among millions of people in many regions of the world, leading to endemic iodine deficiency disorders (IDD) often associated with lower-than-normal thyroid hormone production (Medeiros-Neto, et al., *Thyroid Research*, (Robbins and Braverman, eds.), (1976) p.497, Excerpta Medica, Amsterdam). The translocation of iodide into the thyroid for thyroid hormogenesis involves two separate processes: iodide accumulation and iodide efflux.

Iodide accumulation is the translocation of iodide from the interstitium into the follicular cells across the basolateral plasma membrane. Iodide accumulation is a $Na^+$-dependent active transport process catalyzed by the sodium/iodide symporter, an intrinsic plasma membrane protein located in the basolateral end of thyrocytes that couples the energy released by the inward "downhill" translocation of $Na^+$ down its electrochemical gradient to driving the simultaneous inward "uphill" translocation of iodide against its electrochemical gradient (Carrasco, *Biochim. Biophys. Acta.* 1154:65–82 (1993)). The $Na^+$ gradient acting as a driving force for iodide accumulation is generated by the ouabain-sensitive, $K^+_{OUT}$-activated $Na^+/K^+$ATPase. Thus, $Na^+$-dependent iodide accumulation (i.e. sodium/iodide symport activity) is the first and rate-limiting step in the biosynthesis of thyroid hormones. Sodium/iodide symport activity in the thyroid is characteristically blocked by the competitive inhibitor perchlorate.

Iodide efflux is the transfer of iodide from the cytoplasm of thyrocytes towards the colloid across the apical plasma membrane. Iodide efflux is a passive diffusion mechanism that has been proposed to be mediated by an iodide channel located in the apical membrane of thyrocytes (Nilsson, et al., *Acta Endocrinol* 126:67–74 (1992); Golstein, et al., *Am. J. Physiol.* 263:C590–C5975 (1992)). The colloid, where the large hormone precursor thyroglobulin (Tg) is stored, is located in the follicular lumen, an extracellular compartment. Iodide is ultimately required at the cell/colloid interface because this is the site where, to a large extent, hormone biosynthesis takes place (Werner and Ingbar, supra; Degroot, supra). Accumulated iodide that has reached the cell/colloid interface is oxidized and incorporated into some tyrosyl residues within the Tg molecule in a reaction catalyzed by thyroid peroxidase (TPO), leading to the subsequent coupling of iodotyrosine residues. This incorporation of iodide into organic molecules is called "iodide organification", a reaction pharmacologically blocked by such anti-thyroid agents as 6-n-propyl-2-thiouracil (PTU). All steps in the thyroid hormone biosynthetic pathway are stimulated by thyroid stimulating hormone (TSH) secreted from the pituitary. The effect of TSH results from binding of the hormone to the TSH receptor, which is also located in the basolateral membrane of the follicular cells.

Sodium/iodide symporter confers to the thyroid gland its most readily distinctive functional attribute, i.e. its ability to actively accumulate iodine. Sodium/iodide symporter provides the molecular basis for the thyroidal radioiodide uptake test and for thyroid scintigraphy, two thyroid function tests of considerable value as diagnostic aids in a variety of thyroid pathological conditions (Werner and Ingbar, supra; Degroot, supra). For example, the possible existence of thyroid cancer must be ruled out whenever a thyroid nodule is detected. Thyroid nodules that are determined by scintigraphy to accumulate iodine equally or more efficiently than the normal surrounding tissue are generally benign, while most thyroid cancers display markedly reduced iodine accumulation activity relative to healthy tissue. Still, sodium/iodide symporter is sufficiently active in some thyroid cancers and metastases to render them amenable to treatment with radioiodine (Werner and Ingbar, supra; Degroot, supra). Conversely, large doses of radiation reaching the gland via sodium/iodide symporter in the form of iodine isotopes can cause thyroid cancer. The most dramatic example of this is the alarming rise in the incidence of thyroid cancer cases in Ukraine and Belarus in the wake of the 1986 Chernobyl power plant accident (Likhtarev, et al., *Nature* 375:365 (1995)). In this instance, $^{131}I$ in the nuclear fallout was ingested largely through milk, mostly by young children, and concentrated in the thyroid via sodium/iodide symporter. Among major thyroid proteins involved in hormogenesis, the TSH receptor, Tg and TPO have all been characterized in considerable molecular detail (Parmentier, et al., *Science* 246:1620–1622 (1989); Mercken, et al., *Nature* 316:647–651 (1985); Magnusson, et al., *J. Biol. Chem.* 262:13885–13888 (1987)). Prior to the present invention however, the cDNA encoding sodium/iodide symporter has not been cloned or characterized.

SUMMARY OF THE INVENTION

The present invention provides a purified and isolated nucleic acid encoding sodium/iodide symporter, a vector comprising this nucleic acid and a host cell transformed by this vector. Also provided by the present invention is a nucleic acid probe which hybridizes to nucleic acid encoding sodium/iodide symporter, a mixture of nucleic acid probes each of which hybridizes to nucleic acid encoding sodium/iodide symporter and a kit comprising one or more nucleic acid probes which hybridize to nucleic acid encoding sodium/iodide symporter.

The present invention also provides a method for producing recombinant sodium/iodide symporter comprising growing a host cell transformed with a vector comprising nucleic acid encoding sodium/iodide symporter in culture and recovering sodium/iodide symporter from the culture.

The present invention further provides a purified sodium/iodide symporter or an analogue thereof, an antibody immunoreactive with sodium/iodide symporter or an analogue thereof, and a kit comprising an antibody immunoreactive with sodium/iodide symporter.

The present invention also provides a method for diagnosing a thyroid disorder in a subject comprising detecting one or more mutations in nucleic acid encoding sodium/iodide symporter, a mutated sodium/iodide symporter, or a decreased concentration of sodium/iodide symporter in the subject relative to normal physiological levels of the sodium/iodide symporter.

In addition, the present invention provides a method for treating a thyroid disorder caused by a mutated nucleic acid encoding sodium/iodide symporter comprising introducing nucleic acid encoding sodium/iodide symporter into substantially all of the thyroid cells of the subject such that an amount of the sodium/iodide symporter effective to treat the thyroid disorder is expressed in the thyroid cells.

The present invention also provides a recombinant viral vector capable of introducing nucleic acid encoding sodium/iodide symporter into a target cell such that the target cell expresses sodium/iodide symporter, the vector comprising (a) nucleic acid of or corresponding to at least a portion of the genome of a virus, the portion being capable of infecting the target cell, and (b) nucleic acid encoding a sodium/iodide symporter operably linked to the viral nucleic acid.

The present invention further provides a method for selectively ablating a target tissue in a subject comprising: (a) introducing nucleic acid encoding sodium/iodide symporter into substantially all cells of the target tissue such that the cells exhibit sodium/iodide symport activity; and (b) supplying radioactive iodide to the cells of the target tissue in an amount sufficient to ablate the target tissue upon uptake of the radioactive iodide by the cells.

The present invention also provides a method for identifying an iodide transport protein from non-thyroid tissue comprising contacting nucleic acid from the non-thyroid tissue with a nucleic acid probe made from nucleic acid encoding sodium/iodide symporter and detecting hybridization thereof.

Finally, the present invention provides a non-human, transgenic animal model for a thyroid disorder comprising mutated nucleic acid encoding sodium/iodide symporter incorporated into thyroid cells of the animal.

Additional objects of the invention will be apparent from the description which follows.

BRIEF DESCRIPTION OF THE FIGURES

FIG. 1 is comprised of FIGS. 1A, 1B, 1C and 1D and depicts expression of sodium/iodide symporter in *Xenopus laevis* oocytes and COS cells. In FIGS. 1A, 1B and 1C each bar and experimental point represent the average of >5 oocytes +/– S.E.

FIG. 2 represents complementary nucleotide and deduced amino acid sequences of the rat sodium/iodide symporter cDNA. Nucleotides (SEQ ID NO:1) are numbered in the 5' to 3' direction beginning with the first base of the cloned cDNA. Untranslated sequences are in lower case and translated sequences in upper case letters. The deduced amino acid sequence (SEQ ID NO:2) (single letter code) is shown below the nucleotide sequence. The twelve putative membrane-spanning domains are shaded in grey. Three potential N-linked glycosylation sites are indicated in bold type (positions 225, 485 and 497). One putative intracellular consensus sequence for cAMP-dependent protein kinase A phosphorylation is boxed (positions 549–552). A polyadenylation signal in the 3' untranslated domain is underlined (position 2795).

FIG. 3 is comprised of FIGS. 3A and 3B.

DETAILED DESCRIPTION OF THE INVENTION

Figure 1A:
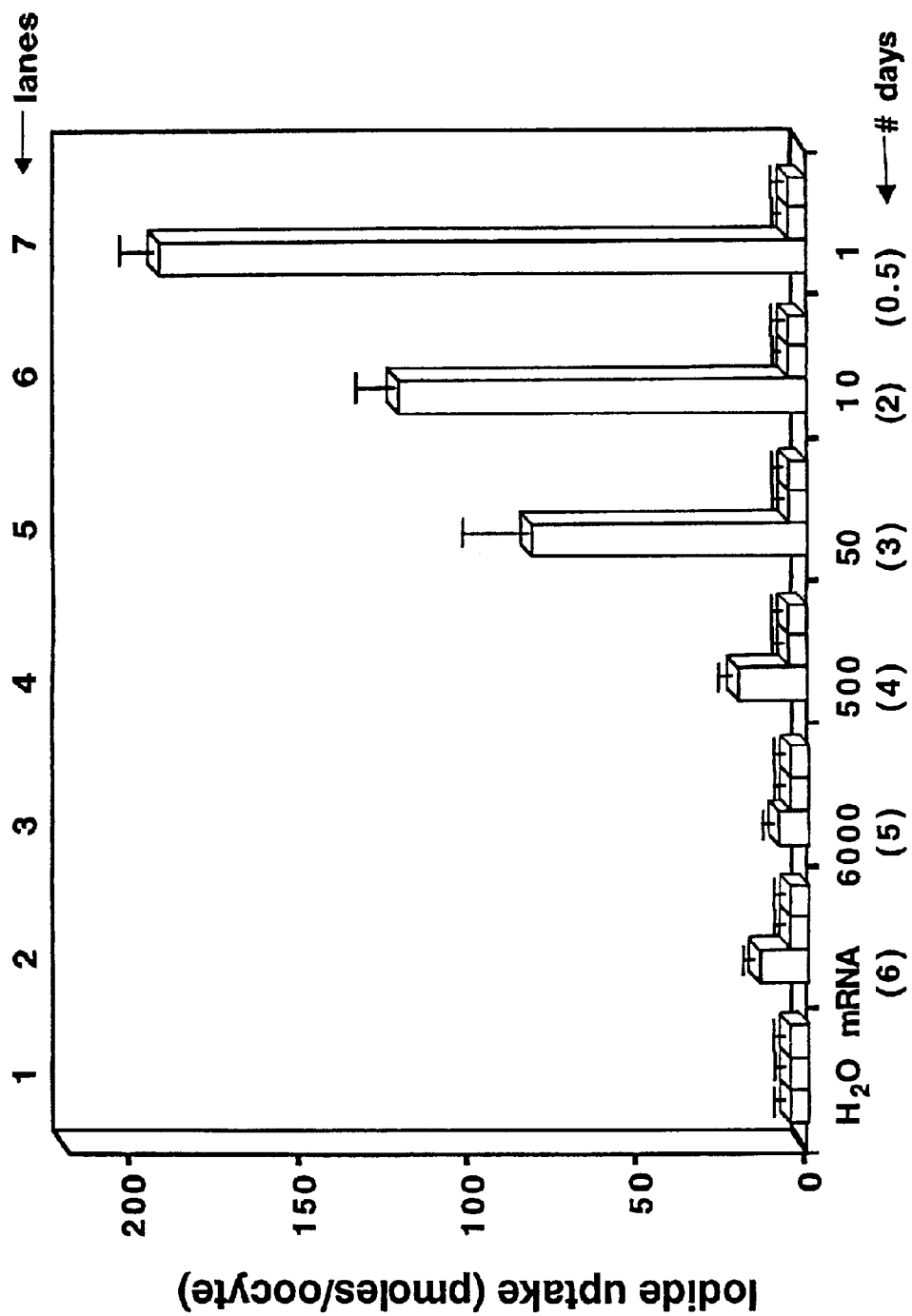
In FIG. 1A oocytes were microinjected with water (lane 1), 50 ng mRNA from FRTL-5 cells (lane 2), or approximately 20 ng cRNA transcripts made in vitro from pools containing the indicated number of cDNA clones (lanes 3–7, numbers without parentheses at bottom of FIG. 1A). Iodide accumulation was assayed in the presence of Na$^+$ (solid bars), absence of Na$^+$ (i.e. in the presence of choline, striped bars), or in the presence of both Na$^+$ and perchlorate (dotted bars) at 45 min, using standard methods (Weiss, et al., *Endocrinology* 114:1090–1098 (1984)). The number of days elapsed after microinjection when sodium/iodide (Na$^+$/I$^-$) symport activity was first detected are indicated in parentheses. Time course (FIG. 1B) and kinetic analysis (FIG. 1C) of iodide accumulation were assessed 60 h after oocytes were microinjected with the transcript from the sodium/iodide symporter cDNA clone.

The present invention provides a purified and isolated nucleic acid encoding sodium/iodide symporter. As used herein, the nucleic acid may be genomic DNA, cDNA, RNA or antisense RNA and includes nucleic acid derived from any species, e.g., human, rat, goat, pig, mouse or cow. Due to the degeneracy of the genetic code, the nucleic acid of the present invention also includes a multitude of nucleic acid substitutions which will encode sodium/iodide symporter.

The present invention also provides a vector which comprises nucleic acid encoding sodium/iodide symporter. Such vectors may be used for storing the nucleic acid encoding sodium/iodide symporter, or for preparing multiple copies of the nucleic acid, as well as producing recombinant sodium/iodide symporter. The vectors may be constructed by inserting nucleic acid encoding sodium/iodide symporter into suitable vector nucleic acid. The term "inserted" as used herein means the ligation of a foreign DNA fragment and vector DNA by techniques such as the annealing of compatible cohesive ends generated by restriction endonuclease digestion or by use of blunt end ligation techniques. Other methods of ligating DNA molecules will be apparent to one skilled in the art.

Vectors may be derived from a number of different sources, e.g., plasmids, viral genomes, lytic bacteriophage derived from phage lambda (λ), cosmids or filamentous single-stranded bacteriophages such as M13. The nucleic acid from which the vector is derived is usually greatly reduced in size so that only those genes essential for its autonomous replication remain. The reduction in size enables the vectors to accommodate large segments of foreign DNA. Examples of suitable vectors for storing or producing multiple copies of the nucleic acid include but are not limited to pBR322, pUC18, pUC19, pHSV106, pJS97, pJS98, M13mp18, M13mp19, pSPORT 1, pGem, pSPORT 2, pSV•SPORT 1, pBluescript II, λZapII, λgt10, λgt11, λgt22A, and λZIPLOX.

Vectors suitable for the expression of the nucleic acid encoding sodium/iodide symporter in a host cell are well known in the art and include pET-3d (Novagen), pProEx-1 (Life Technologies), pFastBac 1 (Life Technologies), pSFV (Life Technologies), pcDNA II (Invitrogen), pSL301 (Invitrogen), pSE280 (Invitrogen), pSE380 (Invitrogen), pSE420 (Invitrogen), pTrcHis A,B,C (Invitrogen), pRSET A,B,C (Invitrogen), pYES2 (Invitrogen), pAC360 (Invitrogen), pVL1392 and pVl1392 (Invitrogen), pCDM8 (Invitrogen), pcDNA I (Invitrogen), pcDNA I(amp) (Invitrogen), pZeoSV (Invitrogen), pcDNA 3 (Invitrogen), pRc/CMV (Invitrogen), pRc/RSV (Invitrogen), pREP4 (Invitrogen), pREP7 (Invitrogen), pREP8 (Invitrogen), pREP9 (Invitrogen), pREP10 (Invitrogen), pCEP4 (Invitrogen), pEBVHis (Invitrogen), and λPop6. Such vectors utilize one of a number of powerful promoters to direct the high level of expression, e.g., the lac operator-promoter or the tac promoter, metallothionine or mouse mammary tumor virus promoters.

Vectors may be introduced into host cells by a number of techniques, e.g. electroporation, DEAE dextran, cationic liposome fusion, protoplast fusion, DNA coated-microprojectile bombardment, and infection with recombinant replication-defective retroviruses. The term "transformation" denotes the introduction of a vector into a bacterial or eukaryotic host cell. As such, it encompasses transformation of bacterial cells and transfection, transduction and related methods in eukaryotic cells.

Any one of a number of suitable bacterial or eukaryotic host cells may be transformed with the vector of the present invention. Examples of suitable host cells are known to one skilled in the art and include but are not limited to bacterial cells such as *E.coli* strains c600, c600hfl, HB101, LE392, Y1090, JM103, JM109, JM101, JM107, Y1088, Y1089, Y1090, Y1090(ZZ), DM1, PH10B, DH11S, DH125, RR1, TB1 and SURE, *Bacillus subtilis, Agrobacterium tumefaciens, Bacillus megaterium;* and eukaryotic cells such as *Pichia pastoris, Chlamydomonas reinhardtii, Cryptococcus neoformans, Neurospora crassa, Podospora anserina, Saccharomyces cerevisiae, Saccharomyces pombe, Uncinula necator,* cultured insect cells, cultured chicken fibroblasts, cultured hamster cells, cultured human cells such as HT1080, MCF7, 143B and cultured mouse cells such as EL4 and NIH3T3 cells.

The present invention also provides a purified sodium/iodide symporter and analogues thereof and includes sodium/iodide symporter isolated from thyroid tissue obtained from a subject or sodium/iodide recombinantly produced. As used herein "analogues" mean amino acid-substituted derivatives of the sodium/iodide symporter which have ability to catalyze the sodium-dependent transport of iodide into a cell.

The present invention also provides for antibodies immunoreactive with sodium/iodide symporter and/or analogues thereof as well as antibodies immunoreactive with non-functional sodium/iodide symporter, i.e., sodium/iodide symporter which is inactive or exhibits only reduced iodine transport activity in vivo. The non-functional sodium/iodide symporter recognized by the antibodies of the present invention may result from one or more mutations in the nucleic acid encoding sodium/iodide symporter or from one or more deficiencies in the cell's protein synthesis and maturation pathways resulting in sodium/iodide symporter which is non-functional due, for example, to altered secondary or tertiary structure. The antibodies of the present invention may be monoclonal or polyclonal and are produced by techniques well known to those skilled in the art, e.g., polyclonal antibody can be produced by immunizing a rabbit, mouse, or rat with purified sodium/iodide symporter and monoclonal antibody may be produced by removing the spleen from the immunized rabbit, mouse or rat and fusing the spleen cells with myeloma cells to form a hybridoma which, when grown in culture, will produce a monoclonal antibody. Labeling of the antibodies of the present invention may be accomplished by standard techniques using one of the variety of different chemiluminescent and radioactive labels known in the art. The antibodies of the present invention may also be incorporated into kits which include an appropriate labeling system, buffers and other necessary reagents for use in a variety of detection and diagnostic applications.

The present invention also provides nucleic acid probes and mixtures thereof which are hybridizable to sodium/iodide symporter. Nucleic acid probes may be prepared by a variety of techniques known to those skilled in the art such as PCR and restriction enzyme digestion of sodium/iodide nucleic acid or by automated synthesis of oligonucleotides whose sequence correspond to selected portions of the nucleotide sequence of the sodium/iodide symporter nucleic acid using commercially available oligonucleotide synthesizers such as the APPLIED BIOSYSTEMS™ Model 392 DNA/RNA synthesizer. The nucleic acid probes of the present invention may also be prepared so that they contain one or more point, insertion or deletion mutations or a combination thereof to correspond to mutations of the sodium/iodide symporter gene.

The nucleic acid probes of the present invention may be DNA or RNA and may vary in length from about 8 nucleotides to the entire length of the sodium/iodide symporter nucleic acid. Labeling of the nucleic acid probes may be accomplished using one of a number of methods known in the art, e.g., PCR, nick translation, end labeling, fill-in end labeling, polynucloetide kinase exchange reaction, random priming, or SP6 polymerase (for riboprobe preparation) and one of a variety of labels, e.g., radioactive labels such as $^{35}S$, $^{32}P$ or $^{3}H$ or nonradioactive labels such as biotin, fluorescein (FITC), acridine, cholesterol or carboxy-X-rhodamine (ROX). Combinations of two or more nucleic probes corresponding to different or overlapping regions of the sodium/iodide symporter nucleic acid may also be included in kits for use in a variety of detection and diagnostic applications.

The present invention also provides methods for diagnosing a thyroid disorder in a subject which is associated with reduced or undetectable iodide transport activity in the subject's thyroid cells. As used herein, "subject" may be a fetus, newborn, infant, child or adult. Reduced or undetectable levels of iodide transport activity in thyroid cells is associated with a number of diseases such as hypothyroidism, hyperthyroidism, thyroid cancer and congenital lack of an iodide transport system. Alterations in iodide transport activity may be due to a decrease in the concentration of sodium/iodide symporter in the thyroid cell or due to the presence of non-functional sodium/iodide symporter.

Thyroid disorders resulting from a decreased concentration of sodium/iodide symporter may be diagnosed by nucleic acid hybridization and/or immunological techniques well known in the art. For example, nucleic acid hybridization studies of mRNA extracted from thyroid cells by sodium/iodide-specific nucleic acid probes can be used to determine the concentration of sodium/iodide symporter mRNA present in the cell and the concentration thus obtained, compared to the value obtained for thyroid cells which exhibit a normal level of iodide transport activity. Isolation of RNA from cells may be accomplished by a number of techniques, e.g., whole cell RNA can be extracted using guanidine thiocyanate; cytoplasmic RNA may be prepared by using phenol extraction methods; and polyadenylated RNA may be selected using oligo-dT cellulose. Alternatively, the concentration of sodium/iodide symporter in the cell may be determined from binding studies using antibody immunoreactive with sodium/iodide symporter.

Thyroid disorders resulting from mutations in the nucleic acid encoding sodium/iodide symporter may be detected by one of a number of methods, e.g., hybridization analysis of nucleic acid extracted from a sample of tissue or cells from a subject's thyroid using nucleic acid probes designed to detect the presence of mutations in the nucleic acid encoding sodium/iodide symporter. Alternatively, the thyroid disorder may be detected using antibody immunoreactive with non-functional sodium/iodide symporter and standard immunological detection techniques such as Western blotting.

The present invention also provides a method for treating a thyroid disorder in a subject which is caused by mutation(s) in the sodium/iodide nucleic acid which encode a non-functional sodium/iodide symporter. The method of the present invention comprises introducing nucleic acid encoding a functional sodium/iodide symporter into substantially all the cells of a subject's thyroid. The nucleic acid encoding the sodium/iodide symporter may be RNA or DNA and may be introduced into the subject's thyroid cells by any one of a number of techniques, e.g., infecting cells with a recombinant viral vector derived from a DNA or RNA virus or a retrovirus which contains nucleic acid encoding a functional sodium/iodide symporter. In the method of the present invention, nucleic acid encoding functional sodium/iodide symporter is introduced into the subject's thyroid cells such that the cells express functional sodium/iodide symporter and are capable of iodide transport activity sufficient to treat the subject's thyroid disorder.

The present invention also provides a recombinant viral vector for use in such applications as gene therapy. The recombinant viral vector of the present invention comprises at least that portion of a viral genome which enables the virus to infect a target cell. In the recombinant viral vector of the present invention the viral nucleic acid sequences are operably linked to nucleic acid encoding sodium/iodide symporter such that, upon introduction of the recombinant viral vector into the target cell, sodium/iodide symporter is expressed in the target cell and the target cell is capable of transporting iodide. The recombinant viral vector of the present invention may further comprise specifically engineered promoter-enhancer sequences to achieve sodium/iodide symporter expression localized to only the target cell and/or a high level of sodium/iodide symporter expression in the target cell. Promoter-enhancer sequences include but are not limited to herpes promoter IE 4/5, cytomegalovirus-1 promoter and the *Rous sarcoma* virus long terminal repeat.

Recombinant viral vectors suitable for gene therapy include but are not limited to vectors derived from the genomes of viruses such as HSV, adenovirus, adeno-associated virus, Semiliki Forest virus, cytomegalovirus and vaccinia virus. Examples of suitable viral vectors for the introduction of sodium/iodide symporter into target cells are HSVprPUC, pZeoSV (Invitrogen), pcDNA3 (Invitrogen), pRc/CMV (Invitrogen), pRc/RSV (Invitrogen), pSVT7 (Life Technologies), p91023(B) (Life Technologies), pMB1 (Clontech), pEUK-C1 (Clontech), pMAMneo (Clontech), pMAMneo-CAT (Clontech), pMAMneo-LUC (Clontech), pDR2 (Clontech), pADα (Clontech), pADβ (Clontech), pCMVβ (Clontech) and pGFP (Clontech). The choice of recombinant viral vector will be determined by the characteristics of the target cell population, e.g., recombinant viral vectors such as those based on adenovirus and herpes virus are suited to target cells which have minimal mitotic activity because these vectors do not integrate into the genome; in contrast, the use of a recombinant viral vector which integrates into the genome such as a vector based on adeno-associated virus is preferred in mitotically active cell populations. Techniques for preparing stocks of recombinant viral vectors are well known in the art and may, for example, require co-infection of a "packaging cell line" with the recombinant viral vector and a helper virus. The helper virus and packaging cell line contain all the genes necessary to replicate the viral vector and package it into virions.

The present invention also provides a method for selectively ablating thyroid or non-thyroid tissue in a subject and may be used to excise inoperable tumors or as a non-invasive alternative to surgery. The method of the present invention involves the introduction of nucleic acid encoding sodium/iodide symporter into substantially all of the cells of a target tissue such that those cells express sodium/iodide symporter and are capable of iodide transport. Methods for introducing sodium/iodide symporter into cells are discussed above. Ablation of the target tissue is accomplished by treating the subject with a radioactive isotope of iodine following introduction of the sodium/iodide symporter. The use of radioisotopes of iodine is well known in the art, e.g., $^{131}$I is the most commonly used isotope in clinical practice. The radioisotope of iodine to be used, its dosage and the means of delivery will be dependent upon a number of factors, e.g., variability in intersubject pharmacokinetic parameters and the type of target tissue, but would be apparent to one skilled in the art. In particular, the method of the present invention may be used to treat thyroid cancer in a subject. The majority of thyroid cancers display markedly reduced iodide transport activity making them resistant to radiotherapy with radioisotopes of iodine. The method of the present invention, by endowing iodide transport activity on the cells of the thyroid tumor thereby restores the use of radioactive iodide as a potentially viable treatment modality.

The present invention also provides a method for identifying an iodide transport protein from non-thyroid tissue including but not limited to the salivary gland, gastric mucosa, lactating mammary gland, choroid plexus and the ciliary body of the eye. Iodide transport proteins from non-thyroid tissues may be identified by a number of techniques known in the art, e.g., screening a cDNA library prepared from the tissue of interest using nucleic acid encoding all or a portion of sodium/iodide symporter as a probe and assessing the ability of cDNA clones thus identified to endow iodide transport activity in COS cells or *Xenopus leavis* oocytes. Labeling of nucleic acid probes has been discussed previously and methods for introducing nucleic acid into COS cells or *Xenopus leavis* oocytes and functional screening are discussed in the Experimental Details Section which follows.

Finally, the method of the present invention provides a non-human, transgenic animal model for a thyroid disorder. The animal model of the present invention comprises a non-human, transgenic animal having nucleic acid encoding mutated sodium/iodide symporter incorporated into thyroid tissue. The mutated nucleic acid encoding sodium/iodide symporter may consist of nucleic acid isolated from the thyroid cells of subjects suffering from thyroid disorders associated with non-functional sodium/iodide symporter.

Nucleic acid encoding mutated sodium/iodide symporter may be integrated into the germ line of a non-human animal such as a mouse, rat, goat, sheep or other species in order to obtain a transgenic animal. Expression of the incorporated nucleic acid may be restricted to the thyroid tissue in the transgenic animal by the utilization of tissue-specific promoters. Methods of making transgenic animals are well known in the art. For example, DNA encoding mutated sodium/iodide symporter can be inserted into the genome of a replication-defective virus such as HSV, or a retrovirus or transposon and the resultant construct injected into embryonic stem cells. Transgenic animals may also be made by injecting DNA encoding mutated sodium/iodide symporter into the male pronucleus of a fertilized egg of a non-human animal, transplanting the "transgenic embryo" into a pseudopregnant female and then analyzing offspring for the presence of the injected DNA in their genome. Other methods of producing transgenic mice would be apparent to one skilled in the art.

The present invention is described in the following Experimental Details Section which is set forth to aid in the understanding of the invention, and should not be construed to limit in any way the invention as defined in the claims which follow thereafter.

Experimental Details Section

1. Materials and Methods

A. Isolation of cDNA Encoding Sodium/Iodide Symporter

A directional cDNA library was prepared in the pSPORT (BRL) vector from poly $A^+$ RNA isolated from FRTL-5 cells. cRNAs were synthesized in vitro using T7 RNA polymerase in the presence of $m^7GpppG$ from pools of cDNA clones. Transcripts were injected into oocytes and oocytes were assayed for perchlorate-sensitive $Na^+/I^-$ symport activity as described in Weiss, et al., supra. Clones from one positive pool were subdivided and assayed successively until a single sodium/iodide symporter cDNA clone was isolated. COS-7 cells were grown in 6-well plates (37° C., 5% $CO_2$) in high glucose Dulbecco's modified Eagles medium (DMEM) supplemented with 10% fetal calf serum. Cells were transfected when they reached approximately 70% density. Cells were rinsed with serum-free medium and incubated with Opti-MEM1 (Gibco) containing 0.5 mg/ml DEAE-Dextran (MW $2\times10^6$) and 0.66 μg/well column-purified (Qiagen) plasmid DNA for 30 min at 37° C., followed by a 3 hr incubation with 0.1 mg/ml chloroquine in DMEM. Iodide accumulation assays were conducted 48 h after transfection using previously described procedures (Kaminsky, et al., supra).

B. Sequence Analysis

Both strands of the sodium/iodide symporter cDNA were sequenced using Sequenase version 2.0 (U.S. Biochemical).

C. Northern Blot Analysis

Thirty μg of total RNA was size fractionated in a denaturing 0.66 M formaldehyde, 1.5% agarose gel (1×MOPS buffer), and transferred to a nylon membrane by overnight capillary blotting in 10×SSC. RNA quality was assessed by ethidium bromide staining. Nylon membranes were hybridized overnight at 42° C. with [$^{32}$P]αdCTP labeled sodium/iodide symporter cDNA in 6×SSC, 5×Denhardt's reagent, 0.5% SDS, 100 μg/ml denatured salmon sperm DNA and 50% formamide. Membranes were washed twice for 30 min at room temperature with 2×SSC/0.1% SDS, and then for 15 min at 55° C. in 0.1% SSC/0.1% SDS. Sodium/iodide symporter and cyclophillin cDNAs were $^{32}$P-dCTP radiolabelled by random primed synthesis (Amersham).

II. Results

A. Isolation and Characterization of the Sodium/Iodide Symporter cDNA Clone

A rat thyroid cDNA library constructed in the pSPORT vector was size fractionated and the fraction containing inserts from 2.5–4.5 kb was subjected to functional screening in oocytes. cRNAs synthesized in vitro from pools of cDNA clones from this fraction were microinjected into oocytes and assayed for perchlorate-sensitive sodium/iodide ($Na^+/I^+$) symport activity. As shown in FIG. 1A, positive pools containing successively fewer cDNA clones were assayed until a single positive clone was identified. Activity elicited by mRNA from FRTL-5 cells is also shown (lane 2). Control assays were carried out in oocytes microinjected with water (lane-1). $Na^+$-dependence was ascertained by using choline in place of $Na^+$, and perchlorate sensitivity was tested by conducting assays in the presence of both $Na^+$ and perchlorate. In all cases, activity measured in the absence of $Na^+$ or in the presence of perchlorate was virtually indistinguishable from background. At the bottom of FIG. 1A the number of clones in each pool tested is shown above the number of days (in parentheses) elapsed after microinjection when $Na^+/I^-$ symport activity was first detected. A clear correspondence is apparent between the decreasing number of clones in the pools, the rising magnitude of the activity elicited, and the shortening of the latency period for appearance of the signal after injection.

Figure 1B:
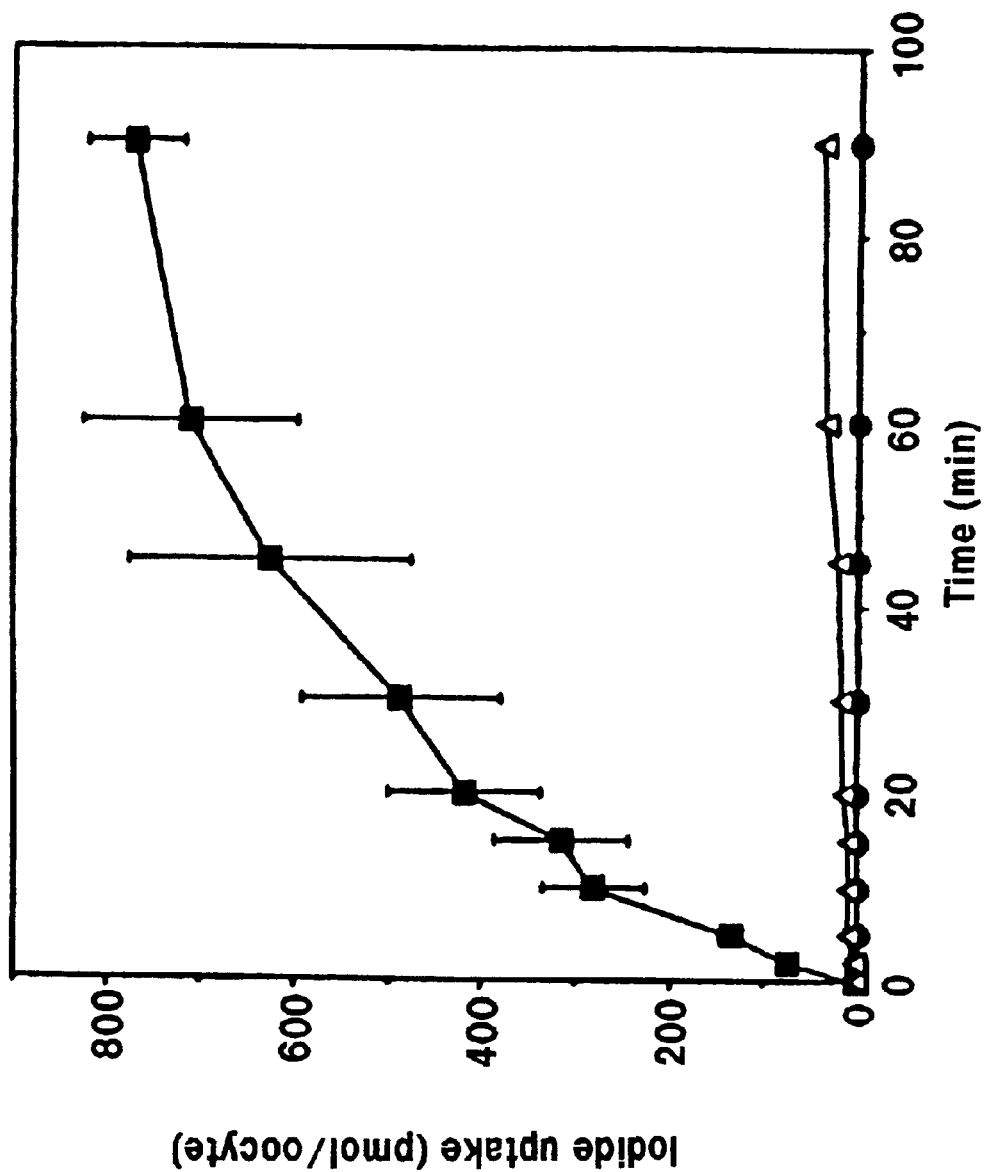
Figure 1C:
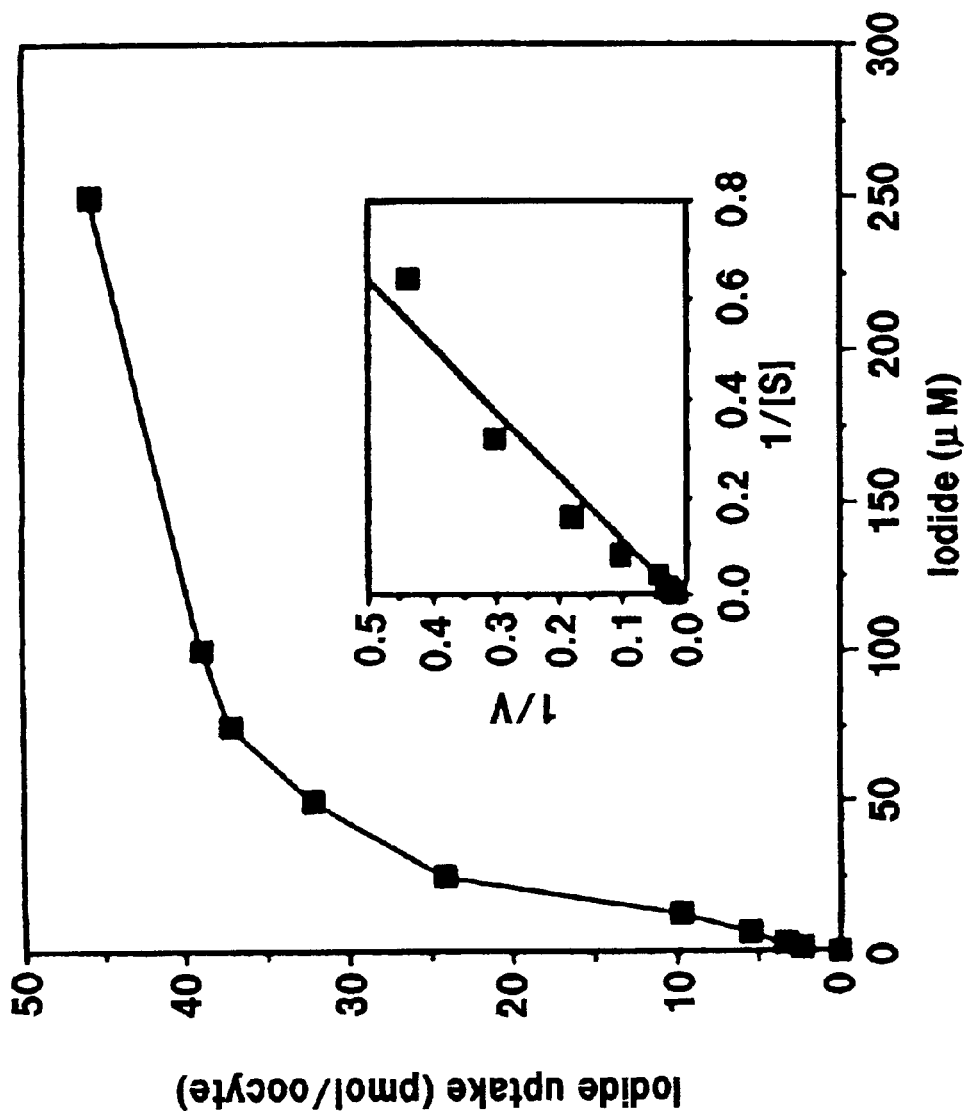
In FIG. 1C, initial velocity rates of Na$^+$/I$^-$-symport activity were determined at the 2 min time points at various iodide concentrations (1.25 to 250 μM). Inset: Double reciprocal plot.
Figure 1D:
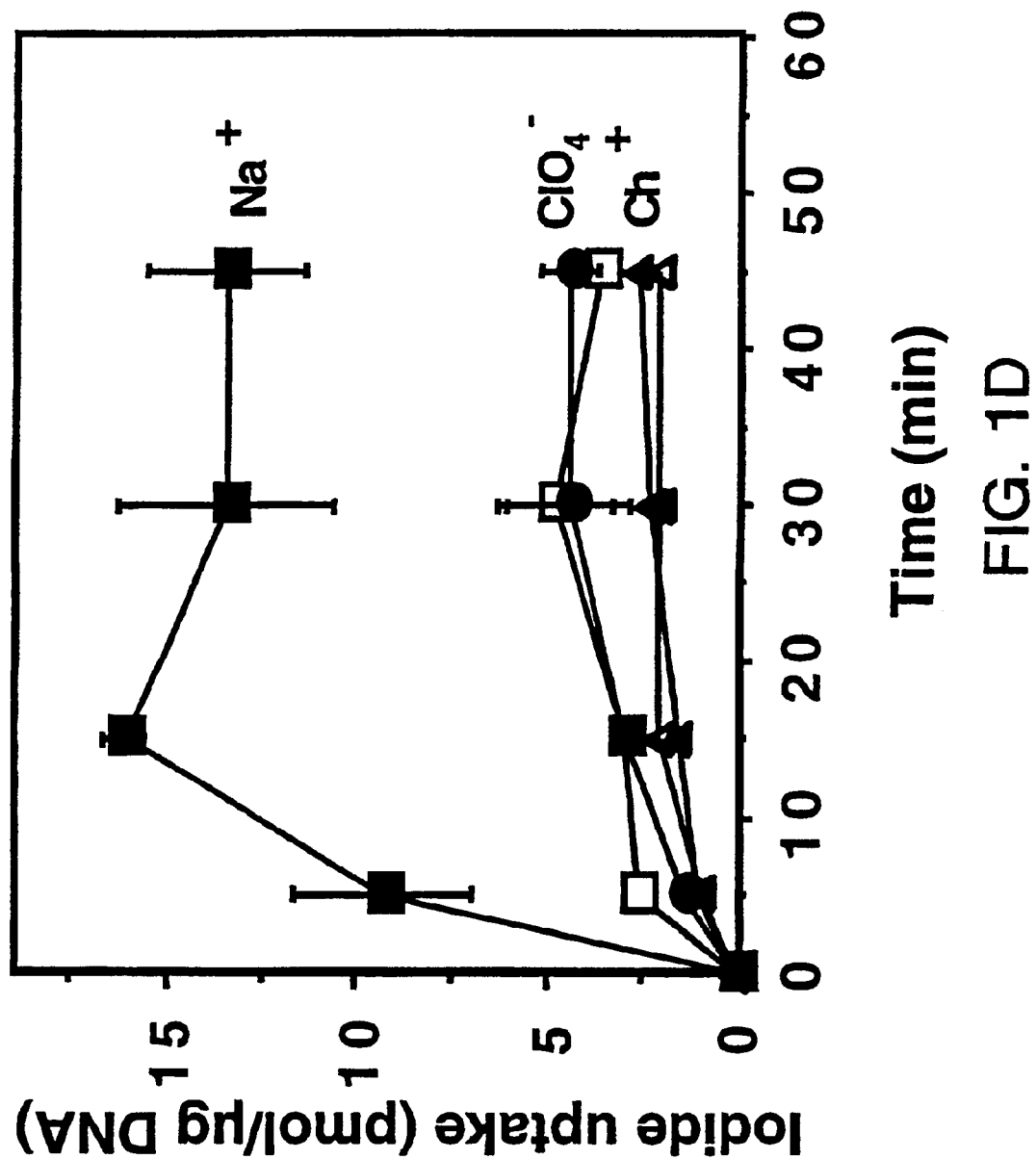
FIG. 1D depicts a time course of iodide accumulation in COS cells transfected with pSV.SPORT plasmid containing sodium/iodide symporter cDNA (continuous lines) or an irrelevant insert (dotted line), or without DNA (dashed line). Iodide accumulation was assayed in the presence of Na$^+$ (■), absence of Na$^+$ (i.e. in the presence of choline, ●), or in the presence of both Na$^+$ and perchlorate (▲ or △) at the indicated time points, as described elsewhere (Kaminsky, et al., *Proc. Nat. Acad. Sci. USA*, 91:3789–3793 (1994)). Each point represents the average of triplicate determinations +/–SE.

Maximal expression of $Na^+/I^-$ symport activity was observed 2–3 days after injection. The time course of iodide accumulation was assessed 60 h after oocytes were injected with the transcript from the sodium/iodide symporter cDNA clone. As shown in FIG. 1B, iodide accumulation reached nearly 800 pmol of iodide/oocyte at the approximately 90 min saturation point. Given that the iodide concentration in the transport solution was 50 μM and the functional volume is 0.5 μl/oocyte, the generated iodide concentration gradient was >30 fold, i.e. virtually identical to that observed in the thyroid gland in vivo (Carrasco, *Biochim. Biophys. Acta.*, supra). This signal corresponds to a >700-fold increase in perchlorate-sensitive $Na^+/I^-$ symport activity over background. The kinetic analysis of $Na^+/I^-$ symport activity in oocytes microinjected with the transcript from the symporter cDNA clone is depicted in FIG. 1C. Initial velocity rates of Na$^+$/I$^-$ symport activity were determined at the 2 min time points at various iodide concentrations (1.25 to 250 μM). Na$^+$/I$^-$ symport rates were found to display saturation kinetics (FIG. 1C). The double reciprocal plot of the same data is shown in the inset. The apparent K$_m$ for iodide was 36 μM, a value consistent with the range of values reported for FRTL-5 cells (Vilijn and Carrasco, *J. Biol. Chem.* 264:11901–11903 (1989); Carrasco, supra). As shown in FIG. 1D, COS cells transfected with the sodium/iodide symporter cDNA clone exhibited perchlorate-sensitive Na$^+$/I$^-$ symport activity, in contrast to control non-transfected cells or cells transfected with the same plasmid containing an irrelevant insert, neither of which displayed symport activity. These results provide unequivocal proof that the product of the sodium/iodide symporter cDNA clone is sufficient to elicit perchlorate-sensitive Na$^+$/I$^-$ symport activity in both oocytes and mammalian cells, and suggest that the symporter functions as a single subunit or as an oligomer of identical subunits.

A nucleic acid contained in the vector pSPORT was identified as containing the entire coding region of the rat sodium/iodide symporter and was designated pNIS. pNIS was deposited under the terms of the Budapest Treaty with the American Tissue Culture Collection (ATCC) located at 10801 University Blvd., Manassas, Va. 20110–2009 on Feb. 1. 1996 under ATCC Designation No. 97431.

Figure 3A:
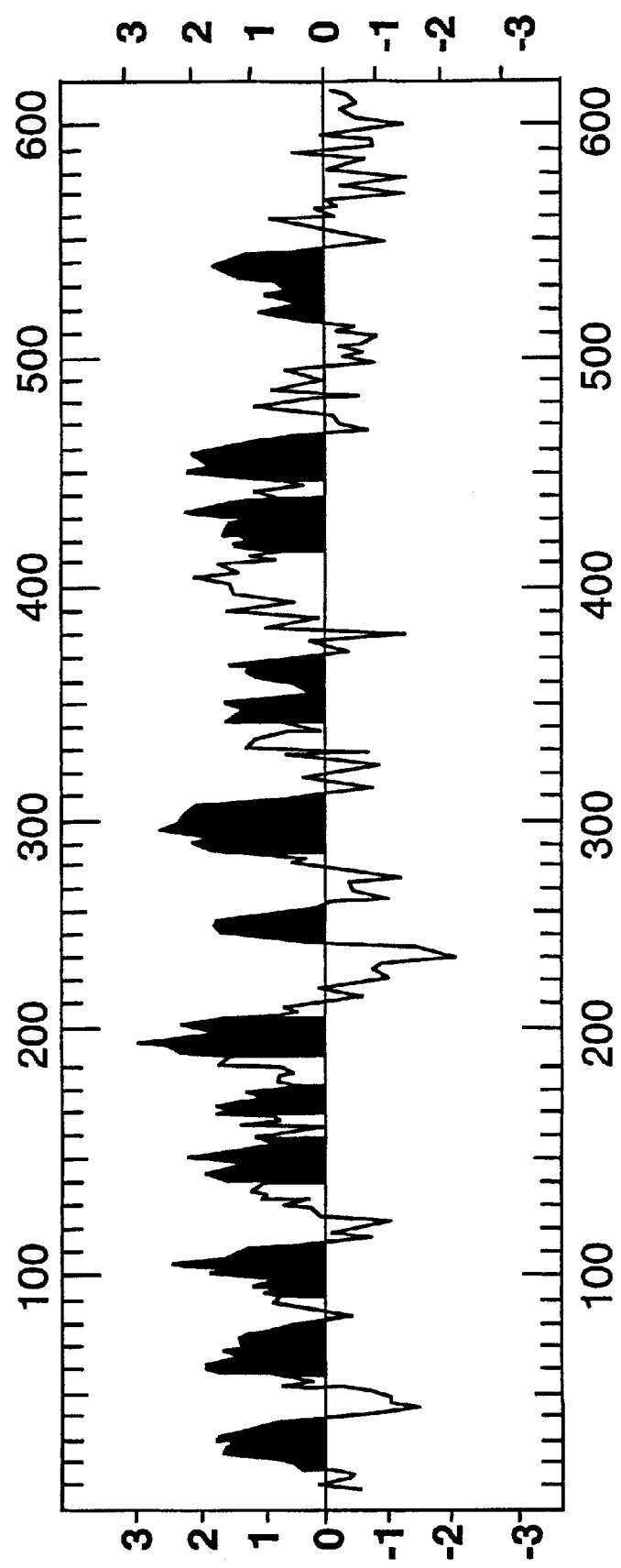
FIG. 3A depicts a hydropathy plot of the deduced amino-acid sequence. The hydropathic analysis was based on the Kyte-Doolittle algorithm (Kyte and Doolittle, *J. Mol. Biol.*, 157: 105–132 (1982)) with a window of 9 residues. Hydropathy values (positive correspond to hydrophobic and negative to hydrophilic regions) are plotted against amino acid position. Putative membrane-spanning domains are shown as filled-in areas under plot line.
Figure 3B:
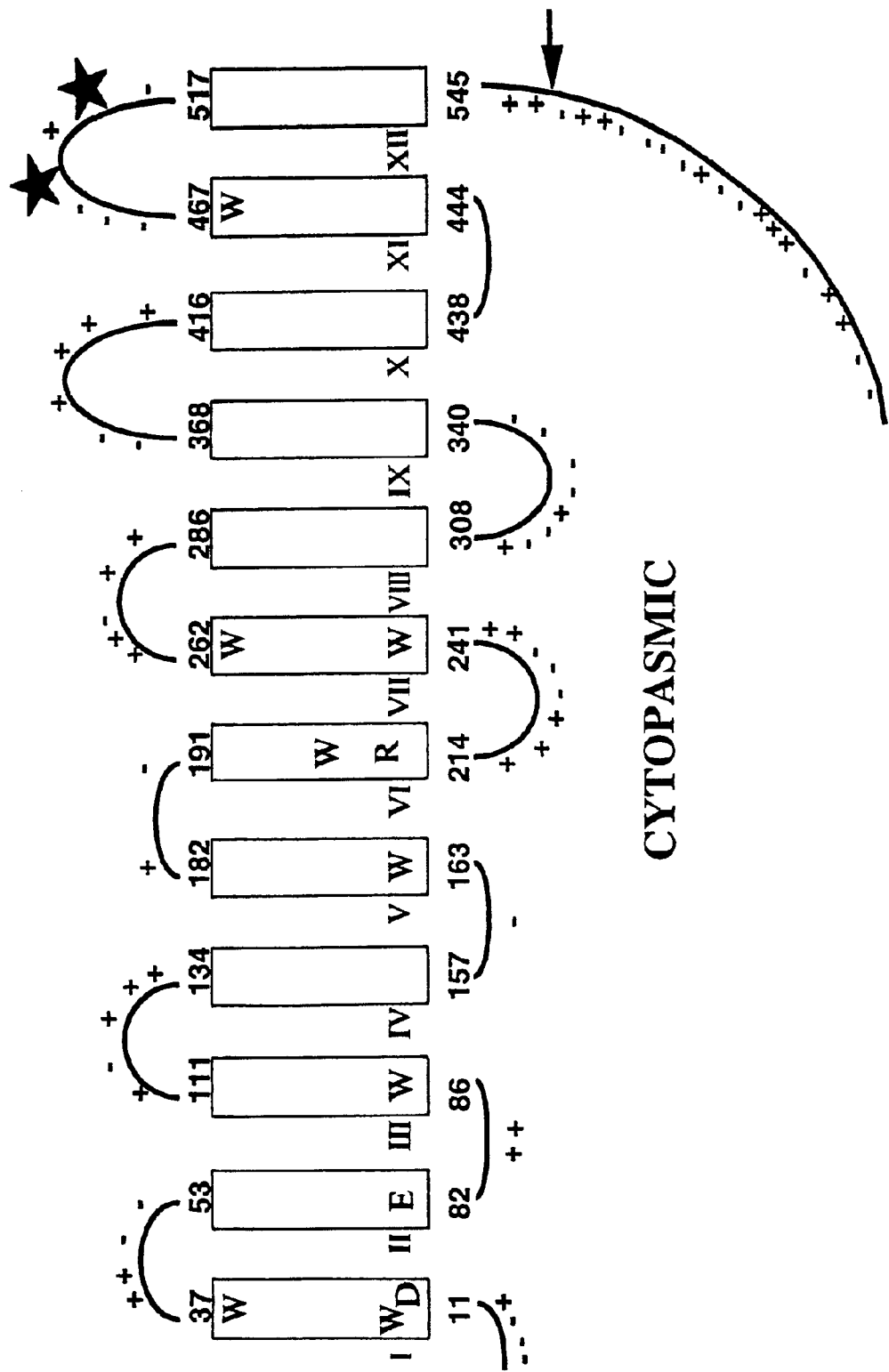
FIG. 3B depicts a schematic representation of the putative topology of the rat sodium/iodide symporter in the membrane. Roman numerals indicate putative membrane-spanning domains. Potential N-linked glycosylation sites are indicated by asterisks. A putative intracellular consensus sequence for cAMP-dependent protein kinase A phosphorylation is indicated with an arrow.
Figure 4:
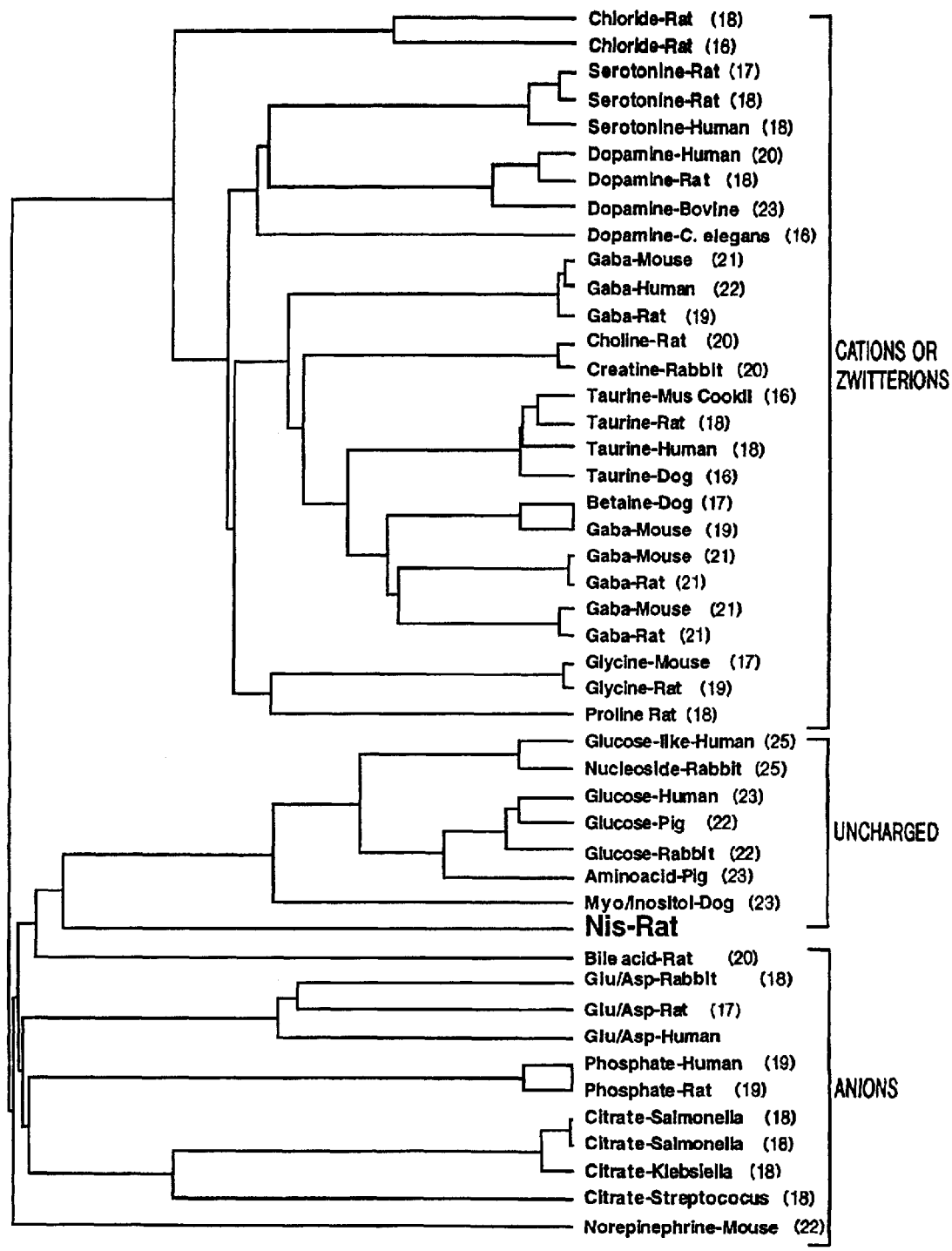
FIG. 4 depicts a dendrogram representing a cluster analysis of members of the Na$^+$-dependent cotransporter protein family. A multiple analysis was created using the PILEUP program of the Genetic Computer Group. The dendrogram is a tree representation of clustering relationships among the deduced amino acid sequences of the cDNAs used for the analysis. The numbers in parentheses represent the percent of homology to the rat sodium/iodide symporter cDNA.

B. Primary Sequence and Predicted Secondary Structure of the Sodium/Iodide Symporter Molecule The complete nucleotide sequence of the cloned sodium/iodide symporter cDNA and the deduced amino acid sequence are presented in FIG. 2. The nucleotide sequence of the sodium/iodide symporter clone indicates that the insert is 2,839 base pairs in length, with a predicted open reading frame of 1854 nucleotides, a 5' untranslated region of 109 nucleotides and a 3' untranslated region of 876 nucleotides. Within the 3' untranslated region, a potential poly A signal was identified at position 2795. The putative initiation codon ATG contains a purine at position 113 and thus represents a reasonable Kozak consensus sequence (Kozak, *J. Biol. Chem.* 266:19867–19870 (1991)). Beginning with Met at position 1, a long open reading frame codes for a protein of 618 amino acids (relative molecular mass 65,196). The hydropathic profile (FIG. 3A) and secondary structure predictions (Kyte and Doolittle, supra; Chou and Fasman, *Biochemistry* 13:222–245 (1974)) (not shown) of the protein suggest that the cloned cDNA encodes for an intrinsic membrane protein with 12 putative transmembrane domains (FIG. 3B). In FIG. 3B the NH$_2$ terminus has been placed on the cytoplasmic side, given the absence of a signal sequence. The COOH terminus, which has also been predicted to be on the cytoplasmic side, contains a large hydrophilic region of approximately 70 amino acids within which the only potential cAMP-dependent PKA phosphorylation domain of the molecule is found (positions 549-552). Three potential Asn-glycosylation sites were identified in the deduced amino acid sequence at positions 225, 485, and 497. The last two are located in the 12th hydrophilic sequence, a domain predicted to be on the extracellular face of the membrane. The length of the 12 transmembrane domains in the model ranges from 20 to 28 amino acid residues, except helix V, which contains 18 residues. Only three charged residues are predicted to lie within transmembrane domains, namely Asp 16 in helix I, Glu 79 in helix II, and Arg 208 in Helix VI. All three charged residues are located close to the cytoplasmic side of the corresponding domain rather than towards its center. Out of a total of 8 Trp residues found in the membrane, six are located near the extremes of transmembrane domains. The lengths of transmembrane domains and location of Trp residues proposed in the sodium/iodide symporter secondary structure model are similar to those found in the *R.viridis* photoreaction center crystal structure (Deisenhofer and Michel, *EMBO J.* 8:2149–2170 (1989)). Four Leu residues (positions 199, 206, 213 and 220) appear to comprise a Leu zipper motif. This motif, which has been proposed to play a role in the oligomerization of subunits in the membrane, has been conserved in all cloned neurotransmitter transporters (Surratt, et al., *Curr.Opin Nephrol.Hypertens* 2:744–760 (1993)). A comparison of the predicted amino acid sequence of sodium/iodide symporter which those of other cloned Na$^+$-dependent cotransporters in available databases (Swissprot.) revealed the highest degree of homology (24.6% amino acid identity) with the human Na$^+$/glucose cotransporter (Hediger, et al., *Proc. Natl. Acad. Sci. USA* 86:5748–5752 (1989)). Sodium/iodide symporter falls alongside other anion transporters in a dendrogram representing a cluster analysis of Na$^+$-dependent cotransporters on the basis of their amino acid sequences (FIG. 4).

A 2.9 kb mRNA transcript that hybridizes with isolated sodium/iodide symporter cDNA clone was identified by Northern analysis (not shown) in both FRTL-5 cells and rat thyroid tissue, but not in such non-thyroid tissues as rat brain, intestine, heart, kidney and liver, thus suggesting that sodium/iodide symporter is primarily expressed in thyroid cells. As expected, the sodium/iodide symporter transcript was more readily detectable in the epithelial cell line than in thyroid tissue.

C. Identification of cDNA Encoding Human Sodium/Iodide Symporter

In order to identify the human sodium/iodide symporter, a cDNA library prepared from human thyroid will be screened using DNA encoding the rat sodium/iodide symporter as a probe. cRNAs will be synthesized in vitro from cDNA clones identified as potentially containing human sodium/iodide symporter-specific sequences in vitro using T7 RNA polymerase in the presence of m$^7$GpppG. Transcripts will be injected into oocytes and oocytes then assayed for perchlorate-sensitive Na$^+$/I$^-$ symport activity.

III. Conclusion

In summary, the rat sodium/iodide symporter cDNA clone has been isolated and a secondary structure model for the sodium/iodide symporter molecule designed. It has been shown that the product of the sodium/iodide symporter cDNA clone is sufficient to elicit Na$^+$/I$^-$ symport activity in both oocytes and mammalian cells, suggesting that sodium/iodide symporter probably functions as a single subunit. The data presented here establish that rat sodium/iodide symporter is a 618 amino acid (relative molecular mass 65,196) Na$^+$-dependent intrinsic membrane protein with 12 putative transmembrane α-helix domains. The role of sodium/iodide symporter as the mediator of iodide accumulation is consistent with its placing alongside other Na$^+$-dependent anion transporters on the basis of clustering relationships between its deduced amino acid sequence and the deduced sequences of other transporters. Given that some of the residues important for function in several membrane transporters are charged amino acids located in putative transmembrane domains (Carrasco, et al. *Biochemistry* 25:4486–4488 (1986); Zhang, et al., *J. Biol. Chem.* 269:19573–19577 (1994); Pantanowitz, et al., *J. Biol. Chem.* 268:3222–3225 (1993)), it is suggested that one or more of the three such residues in sodium/iodide symporter, namely Asp 16, Glu 79 and Arg 208, may play a role in Na$^+$/I$^-$ symport activity. In Northern blot analyses using the sodium/iodide symporter cDNA clone as a probe it was observed that 2.9 kb transcript is present in FRTL-5 cells and in the thyroid gland but not in brain, intestine, heart, kidney or liver.

The cloning and characterization of sodium/iodide symporter constitutes the full molecular identification of the protein that mediates iodide accumulation in the thyroid, i.e. the key initial step in thyroid hormogenesis. A corollary of the present characterization of rat sodium/iodide symporter is that the pathophysiology of the thyroid iodide accumulating system can now be studied at the molecular level. Considering the high degree of homology among eukaryotic transport proteins from different species, it is likely that the human sodium/iodide symporter cDNA clone will be readily isolated in the near future. Hence, it will be possible to explore the expression of human sodium/iodide symporter in such thyroid pathological states as hyper and hypothyroidism, thyroid cancer, and congenital lack of the iodide transport system. The results reported here suggest that elucidation of the molecular mechanism of thyroidal active iodide accumulation and its regulation is within reach.

All publications mentioned hereinabove are hereby incorporated by reference in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method of determining whether a mammalian sodium/iodide symporter is expressed in a mammalian tissue, the method comprising contacting nucleic acid from the mammalian tissue with a probe and detecting whether the probe hybridizes to the nucleic acid, wherein detecting hybridization of the probe to the nucleic acid indicates that the mammalian sodium/iodide symporter is expressed in the mammalian tissue, wherein the probe comprises the nucleic acid sequence comprising nucleotides 110–1963 set forth in SEQ ID NO: 1 or its complement.

2. The method of claim 1, wherein the nucleic acid from the mammalian tissue is mRNA.

3. The method of claim 1, wherein the nucleic acid from the mammalian tissue is mRNA made into cDNA.

4. The method of claim 1, wherein the mammalian tissue is non-thyroid tissue.

5. The method of claim 1, wherein the nucleic acid probe further comprises a label.

6. The method of claim 5, wherein the label is selected from the group consisting of a radioactive label, biotin, and a fluorescent probe.

7. The method of claim 1, wherein the tissue is a human tissue.

8. A method for determining whether a mammalian sodium/iodide symporter is present in a sample, the method comprising contacting the sample with an antibody that is immunoreactive with the mammalian sodium/iodide symporter, wherein detecting binding of the antibody to the mammalian sodium/iodide symporter indicates that the mammalian sodium/iodide symporter is present in the sample, and wherein the antibody is immunoreactive with a protein having the amino acid sequence set forth in SEQ ID NO: 2.

9. The method of claim 8, wherein the antibody is a polyclonal antibody.

10. The method of claim 8, wherein the antibody is a monoclonal antibody.

11. The method of claim 8, wherein the antibody is labeled.

12. The method of claim 8, wherein the sample is a mammalian tissue.

13. The method of claim 12, wherein the mammalian tissue is thyroid tissue.

14. The method of claim 12, wherein the mammalian tissue is non-thyroid tissue.

15. The method of claim 12, wherein the mammalian tissue is human tissue.

* * * * *

UNITED STATES PATENT AND TRADEMARK OFFICE
CERTIFICATE OF CORRECTION

PATENT NO. : 6,803,199 B2  
APPLICATION NO. : 09/995007  
DATED : October 12, 2004  
INVENTOR(S) : Nancy Carrasco, Ge Dai and Orlie Levy Page 1 of 1

It is certified that error appears in the above-identified patent and that said Letters Patent is hereby corrected as shown below:

In the specification

Column 1, lines 8-13, should read:

-- STATEMENT OF GOVERNMENT SUPPORT

This invention was made with government support under grant number DK041544 awarded by the National Institutes of Health. The government has certain rights in the invention. --

Signed and Sealed this  
Third Day of November, 2015

Michelle K. Lee  
*Director of the United States Patent and Trademark Office*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 2839
        (B) TYPE: NUCLEIC ACID
        (C) STRANDEDNESS: DOUBLE
        (D) TOPOLOGY: LINEAR (ii) MOLECULE TYPE: <Unknown>
        (A) DESCRIPTION: OLIGONUCLEOTIDE (iii) HYPOTHETICAL: NO (iv) ANTI-SENSE: NO (vi) ORIGINAL SOURCE:
        (A) ORGANISM: RAT
        (C) INDIVIDUAL ISOLATE: SODIUM/IODIDE SYMPORTER (xi) SEQUENCE DESCRIPTION: SEQ ID NO: 1:

```
GAATTCCGGG TCGACCACGC GTCCGGCGGT GACTCGCGCT GCGACTCTCC                  50

CACTGACCGA GAGTCCCCGA CGTCCTCCGC ATCCTCTCCT CACCGAGTCA                 100

CCTGTCTCC  ATG GAG GGT GCG GAG GCC GGG GCC CGG GCC ACC                 142
           Met Glu Gly Ala Glu Ala Gly Ala Arg Ala Thr
             1               5                      10

TTC GGC GCC TGG GAC TAC GGC GTG TTC GCG ACC ATG CTG CTG                 184
Phe Gly Ala Trp Asp Tyr Gly Val Phe Ala Thr Met Leu Leu
             15                  20                  25

GTG TCC ACG GGC ATC GGG CTA TGG GTC GGC CTG GCC CGC GGT                 226
Val Ser Thr Gly Ile Gly Leu Trp Val Gly Leu Ala Arg Gly
                 30                  35

GGC CAA CGC AGT GCC GAC GAC TTC TTT ACC GGG GGC CGG CAG                 268
Gly Gln Arg Ser Ala Asp Asp Phe Phe Thr Gly Gly Arg Gln
 40                      45                  50

TTG GCA GCC GTT CCT GTG GGG CTG TCG CTG GCC GCC AGT TTC                 310
Leu Ala Ala Val Pro Val Gly Leu Ser Leu Ala Ala Ser Phe
     55                      60                  65

ATG TCG GCT GTG CAG GTG CTC GGG GTC CCC GCC GAG GCA GCG                 352
Met Ser Ala Val Gln Val Leu Gly Val Pro Ala Glu Ala Ala
         70                  75                  80

CGC TAC GGG CTC AAG TTC CTG TGG ATG TGC GCG GGT CAG TTG                 394
```

-continued

```
Arg Tyr Gly Leu Lys Phe Leu Trp Met Cys Ala Gly Gln Leu
            85                  90                  95

CTC AAC TCG CTG CTC ACA GCG TTT CTC TTC TTG CCG ATC TTC          436
Leu Asn Ser Leu Leu Thr Ala Phe Leu Phe Leu Pro Ile Phe
            100                 105

TAC CGC CTG GGC CTT ACC AGC ACC TAC CAG TAC CTA GAG CTG          478
Tyr Arg Leu Gly Leu Thr Ser Thr Tyr Gln Tyr Leu Glu Leu
110                 115                 120

CGC TTC AGC CGA GCG GTC CGG CTC TGC GGG ACG CTG CAG TAC          520
Arg Phe Ser Arg Ala Val Arg Leu Cys Gly Thr Leu Gln Tyr
        125                 130                 135

TTG GTG GCC ACG ATG CTG TAT ACA GGC ATC GTG ATC TAC GCG          562
Leu Val Ala Thr Met Leu Tyr Thr Gly Ile Val Ile Tyr Ala
                140                 145                 150

CCT GCG CTC ATC CTG AAC CAA GTG ACC GGG TTG GAC ATC TGG          604
Pro Ala Leu Ile Leu Asn Gln Val Thr Gly Leu Asp Ile Trp
                    155                 160                 165

GCA TCG CTC CTG TCC ACA GGA ATC ATC TGC ACC TTG TAC ACT          646
Ala Ser Leu Leu Ser Thr Gly Ile Ile Cys Thr Leu Tyr Thr
                        170                 175

ACC GTG GGT GGT ATG AAG GCC GTG GTC TGG ACA GAT GTG TTC          688
Thr Val Gly Gly Met Lys Ala Val Val Trp Thr Asp Val Phe
180                 185                 190

CAG GTT GTG GTA ATG CTC GTT GGC TTC TGG GTG ATC CTG GCC          730
Gln Val Val Val Met Leu Val Gly Phe Trp Val Ile Leu Ala
        195                 200                 205

CGA GGC GTC ATT CTC CTG GGG GGT CCC CGG AAC GTG CTC AGC          772
Arg Gly Val Ile Leu Leu Gly Gly Pro Arg Asn Val Leu Ser
                210                 215                 220

CTC GCT CAG AAC CAT TCC CGG ATC AAC CTG ATG GAC TTT GAC          814
Leu Ala Gln Asn His Ser Arg Ile Asn Leu Met Asp Phe Asp
                    225                 230                 235

CCT GAT CCT CGG AGC CGG TAC ACC TTC TGG ACT TTC ATA GTG          856
Pro Asp Pro Arg Ser Arg Tyr Thr Phe Trp Thr Phe Ile Val
                        240                 245

GGT GGC ACA CTG GTG TGG CTC TCC ATG TAC GGT GTG AAC CAA          898
Gly Gly Thr Leu Val Trp Leu Ser Met Tyr Gly Val Asn Gln
250                 255                 260

GCC CAG GTA CAG CGC TAT GTG GCC TGC CAC ACA GAG GGA AAG          940
Ala Gln Val Gln Arg Tyr Val Ala Cys His Thr Glu Gly Lys
        265                 270                 275

GCC AAA CTG GCC CTG CTT GTC AAC CAG CTG GGC CTC TTC CTG          982
Ala Lys Leu Ala Leu Leu Val Asn Gln Leu Gly Leu Phe Leu
                280                 285                 290

ATT GTG GCC AGT GCA GCT TGC TGT GGC ATT GTC ATG TTC GTC         1024
Ile Val Ala Ser Ala Ala Cys Cys Gly Ile Val Met Phe Val
                    295                 300                 305

TAC TAC AAG GAC TGT GAC CCC CTC CTC ACA GGC CGT ATC TCA         1066
Tyr Tyr Lys Asp Cys Asp Pro Leu Leu Thr Gly Arg Ile Ser
                        310                 315

GCC CCC GAC CAG TAC ATG CCG CTG CTT GTG TTG GAC ATT TTT         1108
Ala Pro Asp Gln Tyr Met Pro Leu Leu Val Leu Asp Ile Phe
320                 325                 330

GAG GAT CTG CCC GGG GTC CCC GGG CTC TTC CTG GCC TGT GCC         1150
Glu Asp Leu Pro Gly Val Pro Gly Leu Phe Leu Ala Cys Ala
        335                 340                 345

TAC AGT GGC ACC CTC AGC ACT GCA TCC ACC AGC ATC AAC GCC         1192
Tyr Ser Gly Thr Leu Ser Thr Ala Ser Thr Ser Ile Asn Ala
                350                 355                 360
```

```
ATG GCA GCT GTG ACT GTG GAA GAC CTC ATC AAG CCG AGG ATG             1234
Met Ala Ala Val Thr Val Glu Asp Leu Ile Lys Pro Arg Met
            365                 370                 375

CCT GGC CTG GCA CCT CGG AAG TTG GTT TTC ATC TCT AAA GGG             1276
Pro Gly Leu Ala Pro Arg Lys Leu Val Phe Ile Ser Lys Gly
                380                 385

CTC TCA TTC ATC TAC GGC TCT GCC TGC CTC ACT GTG GCT GCT             1318
Leu Ser Phe Ile Tyr Gly Ser Ala Cys Leu Thr Val Ala Ala
390                 395                 400

CTG TCC TCA CTG CTG GGA GGT GGT GTC CTC CAG GGT TCC TTC             1360
Leu Ser Ser Leu Leu Gly Gly Gly Val Leu Gln Gly Ser Phe
            405                 410                 415

ACT GTG ATG GGT GTC ATC AGT GGG CCT CTA CTA GGC GCC TTC             1402
Thr Val Met Gly Val Ile Ser Gly Pro Leu Leu Gly Ala Phe
                420                 425                 430

ACG CTT GGG ATG CTG CTC CCA GCC TGC AAC ACG CCA GGC GTT             1444
Thr Leu Gly Met Leu Leu Pro Ala Cys Asn Thr Pro Gly Val
        435                 440                 445

CTC TCC GGG TTG GCA GCA GGC TTG GCT GTA TCC CTG TGG GTG             1486
Leu Ser Gly Leu Ala Ala Gly Leu Ala Val Ser Leu Trp Val
            450                 455

GCC GTA GGG GCC ACA CTG TAT CCC CCT GGA GAG CAG ACC ATG             1528
Ala Val Gly Ala Thr Leu Tyr Pro Pro Gly Glu Gln Thr Met
460                 465                 470

GGG GTG CTG CCC ACC TCG GCT GCA GGC TGC ACC AAC GAT TCG             1570
Gly Val Leu Pro Thr Ser Ala Ala Gly Cys Thr Asn Asp Ser
        475                 480                 485

GTC CTC CTG GGC CCA CCT GGA GCC ACC AAC GCT TCC AAC GGG             1612
Val Leu Leu Gly Pro Pro Gly Ala Thr Asn Ala Ser Asn Gly
            490                 495                 500

ATC CCC AGT TCT GGA ATG GAC ACG GGC CGC CCT GCC CTC GCT             1654
Ile Pro Ser Ser Gly Met Asp Thr Gly Arg Pro Ala Leu Ala
                505                 510                 515

GAT ACC TTT TAC GCC ATC TCC TAT CTC TAT TAC GGG GCT CTG             1696
Asp Thr Phe Tyr Ala Ile Ser Tyr Leu Tyr Tyr Gly Ala Leu
                520                 525

GGC ACG CTG ACC ACC ATG CTT TGC GGT GCT CTC ATC AGC TAC             1738
Gly Thr Leu Thr Thr Met Leu Cys Gly Ala Leu Ile Ser Tyr
530                 535                 540

CTT ACT GGT CCC ACC AAG CGC AGC TCC CTG GGT CCC GGA TTG             1780
Leu Thr Gly Pro Thr Lys Arg Ser Ser Leu Gly Pro Gly Leu
        545                 550                 555

CTG TGG TGG GAC CTT GCT CGA CAG ACA GCG TCT GTG GCC CCA             1822
Leu Trp Trp Asp Leu Ala Arg Gln Thr Ala Ser Val Ala Pro
            560                 565                 570

AAG GAA GAC ACT GCC ACC CTG GAG GAG AGC CTG GTG AAG GGA             1864
Lys Glu Asp Thr Ala Thr Leu Glu Glu Ser Leu Val Lys Gly
                575                 580                 585

CCG GAA GAC ATC CCT GCT GTG ACC AAG AAG CCC CCT GGC CTC             1906
Pro Glu Asp Ile Pro Ala Val Thr Lys Lys Pro Pro Gly Leu
                590                 595

AAG CCA GGC GCC GAG ACC CAC CCC CTG TAT CTG GGG CAC GAT             1948
Lys Pro Gly Ala Glu Thr His Pro Leu Tyr Leu Gly His Asp
600                 605                 610

GTG GAG ACC AAC CTC TGAGGGCGGG GTCCAAGAAG GCCAATCACA                1993
Val Glu Thr Asn Leu
            615

GGCCTCGGGC CAGCAGCCTC CTCTCTGGAT GGTTGGACCT GAGCATATAT              2043

AGAAGCTTGG CTGATACATG CCCTGCCCAG AAGTCCCTGT GTCTTACCCG              2093
```

-continued

```
CACCAAAGAG AGAGAGAGAG AGAGAGAGAG AGAGAGAGAG AGAGAGAGAG        2143

GAGTTGGTTC TCCATCCACA AAGGAAACCG TCTGGAACCT TCATGCCCTT        2193

GTAGATTTCA GTAGGCAGCG GAGAACACTC AGCTTCTCCA GACTGAGGTT        2243

TTCTCATTTA TCAGGCAGAG AAACGGAGGG CTGTCACCCC AACACCGGGG        2293

AGGAGACAGT AGAAGGGTCA TAGATACAAA GAAAACTAAG GCAGAGGGAG        2343

AAATGAATTG TCTACAGAGC ACAGAGCTCC AAGGATTGTG AAGCTACCTT        2393

GAGGTGCCAA GGGACGGATT CTCAGAGCCT TCACAAGACA CAAACGGACG        2443

AGTTGCCTCC TCCAATTCAG ATGGTTTGCA GACTATCAGA GAACATGTTT        2493

CTCCTGTGAT CAGCTACCTA GCCTCTGCCA ACGTGTTCCA GCTTCCAGGA        2543

GGCCACACAG ACCCCACCCC CCATGCTCTC ACCCTTTACC CCTGTGCTTT        2593

TCACACACTA GGCAACTGCT CCACCACAGG ACCTCACACC TAGACCTCCG        2643

TTTTTGACAC AGGGCCTTAA GGTAATCTGG CTGCCATCTG ACTATCTCTC        2693

AGCACGTTCA CGTGTACAAT ATTTCATTCT TTTTCATTGC CAAGTTGTCT        2743

TGTAAGGAGA GACCACAATG TGTCATCCAT GCCCAGCTTT TGTGTCTAAC        2793

AAATAAAATC GCTGAAGGTG TTCAGGTGCA ATGGCCTGTG ACATTA           2839
```

(2) INFORMATION FOR SEQ ID NO: 2:

(i) SEQUENCE CHARACTERISTICS:
  (A) LENGTH: 618
  (B) TYPE: AMINO ACID
  (D) TOPOLOGY: LINEAR (ii) MOLECULE TYPE: <Unknown>
  (A) DESCRIPTION: PROTEIN (iii) HYPOTHETICAL: YES (vi) ORIGINAL SOURCE:
  (A) ORGANISM: RAT
  (C) INDIVIDUAL ISOLATE: SODIUM/IODIDE SYMPORTER (xi) SEQUENCE DESCRIPTION: SEQ ID NO: 2:

```
        Met Glu Gly Ala Glu Ala Gly Ala Arg Ala Thr
         1               5                  10

Phe Gly Ala Trp Asp Tyr Gly Val Phe Ala Thr Met Leu Leu
             15                  20                  25

Val Ser Thr Gly Ile Gly Leu Trp Val Gly Leu Ala Arg Gly
                 30                  35

Gly Gln Arg Ser Ala Asp Asp Phe Phe Thr Gly Gly Arg Gln
40                  45                  50

Leu Ala Ala Val Pro Val Gly Leu Ser Leu Ala Ala Ser Phe
     55                  60                  65

Met Ser Ala Val Gln Val Leu Gly Val Pro Ala Glu Ala Ala
         70                  75                  80

Arg Tyr Gly Leu Lys Phe Leu Trp Met Cys Ala Gly Gln Leu
             85                  90                  95

Leu Asn Ser Leu Leu Thr Ala Phe Leu Phe Leu Pro Ile Phe
                 100                 105

Tyr Arg Leu Gly Leu Thr Ser Thr Tyr Gln Tyr Leu Glu Leu
110                 115                 120

Arg Phe Ser Arg Ala Val Arg Leu Cys Gly Thr Leu Gln Tyr
     125                 130                 135
```

```
Leu Val Ala Thr Met Leu Tyr Thr Gly Ile Val Ile Tyr Ala
            140                 145                 150

Pro Ala Leu Ile Leu Asn Gln Val Thr Gly Leu Asp Ile Trp
            155                 160                 165

Ala Ser Leu Leu Ser Thr Gly Ile Ile Cys Thr Leu Tyr Thr
            170                 175

Thr Val Gly Gly Met Lys Ala Val Val Trp Thr Asp Val Phe
180                 185                 190

Gln Val Val Met Leu Val Gly Phe Trp Val Ile Leu Ala
            195                 200                 205

Arg Gly Val Ile Leu Leu Gly Gly Pro Arg Asn Val Leu Ser
            210                 215                 220

Leu Ala Gln Asn His Ser Arg Ile Asn Leu Met Asp Phe Asp
            225                 230                 235

Pro Asp Pro Arg Ser Arg Tyr Thr Phe Trp Thr Phe Ile Val
            240                 245

Gly Gly Thr Leu Val Trp Leu Ser Met Tyr Gly Val Asn Gln
250                 255                 260

Ala Gln Val Gln Arg Tyr Val Ala Cys His Thr Glu Gly Lys
            265                 270                 275

Ala Lys Leu Ala Leu Leu Val Asn Gln Leu Gly Leu Phe Leu
            280                 285                 290

Ile Val Ala Ser Ala Ala Cys Cys Gly Ile Val Met Phe Val
            295                 300                 305

Tyr Tyr Lys Asp Cys Asp Pro Leu Leu Thr Gly Arg Ile Ser
            310                 315

Ala Pro Asp Gln Tyr Met Pro Leu Leu Val Leu Asp Ile Phe
320                 325                 330

Glu Asp Leu Pro Gly Val Pro Gly Leu Phe Leu Ala Cys Ala
            335                 340                 345

Tyr Ser Gly Thr Leu Ser Thr Ala Ser Thr Ser Ile Asn Ala
            350                 355                 360

Met Ala Ala Val Thr Val Glu Asp Leu Ile Lys Pro Arg Met
            365                 370                 375

Pro Gly Leu Ala Pro Arg Lys Leu Val Phe Ile Ser Lys Gly
            380                 385

Leu Ser Phe Ile Tyr Gly Ser Ala Cys Leu Thr Val Ala Ala
390                 395                 400

Leu Ser Ser Leu Leu Gly Gly Val Leu Gln Gly Ser Phe
            405                 410                 415

Thr Val Met Gly Val Ile Ser Gly Pro Leu Leu Gly Ala Phe
            420                 425                 430

Thr Leu Gly Met Leu Leu Pro Ala Cys Asn Thr Pro Gly Val
            435                 440                 445

Leu Ser Gly Leu Ala Ala Gly Leu Ala Val Ser Leu Trp Val
            450                 455

Ala Val Gly Ala Thr Leu Tyr Pro Pro Gly Glu Gln Thr Met
460                 465                 470

Gly Val Leu Pro Thr Ser Ala Ala Gly Cys Thr Asn Asp Ser
            475                 480                 485

Val Leu Leu Gly Pro Pro Gly Ala Thr Asn Ala Ser Asn Gly
            490                 495                 500
```

-continued

```
Ile Pro Ser Ser Gly Met Asp Thr Gly Arg Pro Ala Leu Ala
            505                 510                 515

Asp Thr Phe Tyr Ala Ile Ser Tyr Leu Tyr Tyr Gly Ala Leu
            520                 525

Gly Thr Leu Thr Thr Met Leu Cys Gly Ala Leu Ile Ser Tyr
530             535                 540

Leu Thr Gly Pro Thr Lys Arg Ser Ser Leu Gly Pro Gly Leu
    545             550                     555

Leu Trp Trp Asp Leu Ala Arg Gln Thr Ala Ser Val Ala Pro
        560             565                 570

Lys Glu Asp Thr Ala Thr Leu Glu Glu Ser Leu Val Lys Gly
            575             580                 585

Pro Glu Asp Ile Pro Ala Val Thr Lys Lys Pro Pro Gly Leu
            590                 595

Lys Pro Gly Ala Glu Thr His Pro Leu Tyr Leu Gly His Asp
600                 605             610

Val Glu Thr Asn Leu
    615
```